United States Patent [19]

Bellhouse et al.

[11] Patent Number: 4,844,097
[45] Date of Patent: Jul. 4, 1989

[54] APPARATUS AND METHOD FOR TESTING LIQUIDS

[75] Inventors: Brian J. Bellhouse; Sydney M. Pugh, both of Oxfordshire, England

[73] Assignee: Bellhouse Technology Limited, Oxford, England

[21] Appl. No.: 6,653

[22] PCT Filed: May 21, 1986

[86] PCT No.: PCT/GB86/00286

§ 371 Date: Feb. 9, 1987

§ 102(e) Date: Feb. 9, 1987

[87] PCT Pub. No.: WO86/07150

PCT Pub. Date: Dec. 4, 1986

[30] Foreign Application Priority Data

May 21, 1985 [GB] United Kingdom ............. 8512796

[51] Int. Cl.[4] .............................................. A61B 5/05
[52] U.S. Cl. ...................................... 128/635; 128/637; 604/4; 422/68; 436/68
[58] Field of Search ............... 422/68.01–68.07; 436/68, 150, 151, 175; 204/1 P, 415; 128/635, 637; 604/4

[56] References Cited

U.S. PATENT DOCUMENTS

| | | | |
|---|---|---|---|
| 3,580,239 | 10/1969 | Watanabe et al. | 128/635 |
| 3,607,084 | 9/1971 | Mackey et al. | 436/178 X |
| 4,003,705 | 1/1977 | Buzza et al. | 23/230 |
| 4,025,308 | 5/1977 | Holman et al. | 436/150 X |
| 4,170,523 | 10/1979 | Buzza et al. | 204/415 X |
| 4,221,567 | 9/1980 | Clark et al. | 23/230 |
| 4,224,125 | 9/1980 | Nakamura et al. | 204/415 X |
| 4,280,505 | 7/1981 | Dali et al. | 128/635 |
| 4,318,884 | 3/1982 | Suzuki | 422/63 |
| 4,324,256 | 4/1982 | Vesterager | 128/635 |
| 4,409,980 | 10/1983 | Yano et al. | 128/635 |
| 4,440,620 | 4/1984 | Ono et al. | 128/635 |
| 4,490,234 | 12/1984 | Buzza | 204/415 X |
| 4,508,598 | 4/1985 | Giner | 128/635 |
| 4,685,465 | 8/1987 | Klitgaard et al. | 128/635 |
| 4,721,677 | 1/1988 | Clark, Jr. | 128/635 |

FOREIGN PATENT DOCUMENTS 2017931 10/1979 United Kingdom .
8303006 9/1983 World Int. Prop. O. .

Primary Examiner—Barry S. Richman
Assistant Examiner—Timothy M. McMahon
Attorney, Agent, or Firm—Jeffers, Hoffman & Niewyk

[57] ABSTRACT

The application relates to a method and apparatus for testing the concentration of a selected atomic scale species in a thick liquid, such as blood. The blood flows through a chamber that is in part defined by a microporous dialysis membrane permeable to atomic scale species. A measuring cell including a second chamber filled with a clean liquid is defined by the other plane of the membrane. The measuring cell incorporates a sensor having an electrode coated with a material permeable only to a selected ionic species.

20 Claims, 1 Drawing Sheet

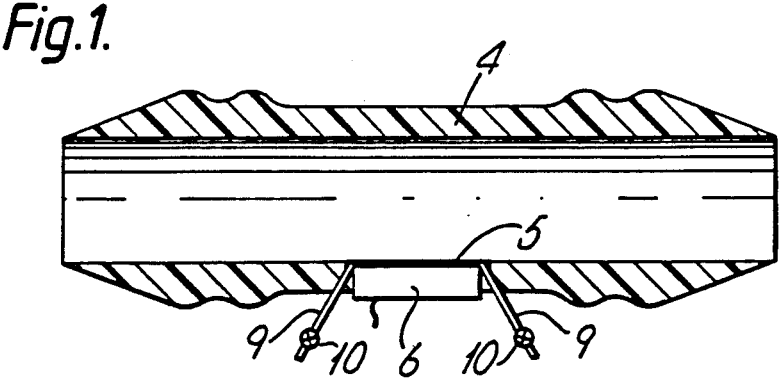
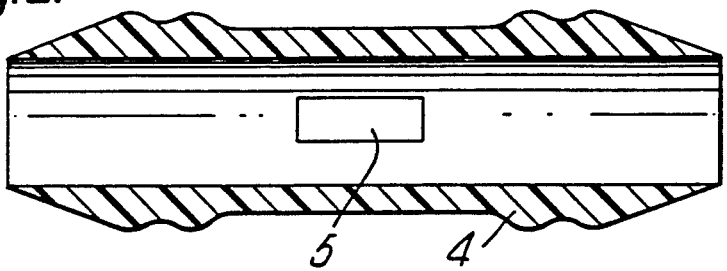
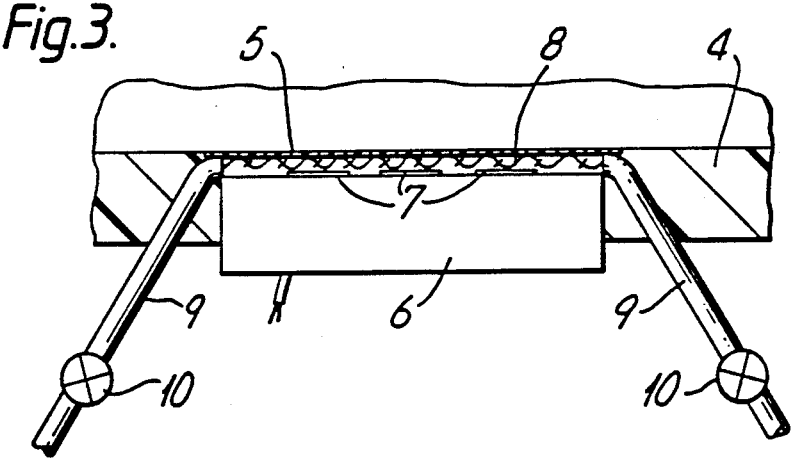

APPARATUS AND METHOD FOR TESTING LIQUIDS

There is a need, for example during operations involving heart-lung bypass, in prolonged respiratory support in acute respiratory failure or in kidney dialysis, to provide an accurate measurement of the concentration of certain gases and electrolytes in the blood. In essence this involves measuring the concentration of "atomic scale species", which in the present context means dissolved atoms and molecules of gases or charged ions. Conventionally such measurements are carried out by taking a sample of the blood, transferring it to a measuring cell, and effecting the measurement. An example of this in vitro technique is disclosed in WO-A-83/03006 in which a blood sample is removed, mixed with an acid reagent and placed in communication with an electrolyte in a measuring cell through a membrane permeable only to a gas derived from the species under test. This is inconvenient as the blood circuit has to be opened to take the sample, the sample taken is wasted, and there is inevitable delay in obtaining the required measurement.

Recently, coatings have been developed which are permeable to selected ions and it has been suggested that the concentration of ions in blood might be monitored continuously by exposing the gate electrode of an ion sensitive field effect transistor (ISFET), which electrode is protected with an appropriate coating permeable to a selected ion, in a blood chamber, and sensing the concentration of the ion by virtue of the corresponding conductivity of the ISFET. Although this technique would enable continuous monitoring of the concentration in the blood of the selected ion, it has the disadvantage that the ion selective coating itself quickly becomes coated with protein and other blood components, thus reducing its permeability to the selected ion. As a result the life of the apparatus is short and frequent recalibration of the ISFET is necessary. Recalibration involves purging the chamber of blood and refilling it with a calibrating liquid of which the concentration of the selected ion is known. The technique therefore requires frequent interruption of the blood flow through the chamber.

Similar problems would arise if the technique were to be used for measuring the concentration of atomic scale species in other liquids, such a milk or liquids used in biotechnological processes, e.g. cell culture and fermentation, as these liquids, like blood, contain components which would be deposited on, and foul, sensitive surfaces. Such liquids are hereinafter referred to as "thick liquids".

In accordance with the present invention, apparatus for testing the concentration of a selected atomic scale species in a thick liquid comprises a first chamber which contains, in use, the thick liquid under test, the chamber being a least partly defined by one face of a microporous membrane which is permeable to atomic scale species; and a measuring cell incorporating a second chamber which is arranged to be filled with a clean liquid and which is at least partly defined by the opposite face of the membrane whereby atomic scale species in the thick liquid under test diffuse through the membrane and are present in the clean liquid in a concentration related to that at which they exist in the thick liquid under test; the cell also incorporating a sensing device which is responsive substantially only to the selected species and which has an electrode or other sensor in communication with the clean liquid in the second chamber whereby the device provides an output related to the concentration of the selected species.

In this context the term "clean liquid" means a liquid which substantially does not inhibit the response of the sensor to the selected species with which it is, in use, in communication. In practice the clean liquid may be distilled water, preferably containing a concentration of the species similar to that which is to be expected in the thick liquid under test.

An advantage of this apparatus is that it is substantially non-invasive and may operate attached to, e.g. a blood circuit without blood loss from, or interruption in the blood flow in, the circuit. For example the first chamber may be a blood conduit, such as a standard blood line connector, having in its wall a hole which is spanned by the microporous membrane. The cell would then be mounted on the outside of the connector overlying the membrane.

In use the microporous membrane will be permeable to a multitude of atomic scale species but substantially not to potentially depositable components in the thick liquid, such as protein and other blood components in the case of blood, which are thus kept away form the interior of the cell and particularly from the active surface of the sensor.

The second chamber in the cell will periodically be flushed through with a calibrating liquid for recalibration of the sensing device and for this purpose the second chamber will be provided with inlet and outlet ducts which are preferably closable to seal the interior of the cell during a test. The response time of the apparatus depends upon the time for the selected species to diffuse through the microporous membrane and throughout the clean liquid in the second chamber until the concentration of the selected species in the clean liquid approaches dynamic equilibrium with that in the thick liquid on the other side of the membrane. Diffusion times are proportional to the square of the distance travelled and consequently the width of the second chamber between the microporous membrane and the active surface of the sensor, which are preferably facing one another, should be as short as possible. A dimension of 0.1 mm has been found to lead to very acceptable response times of the order of between 5 and 15 seconds. This spacing may be achieved by providing a spacer formed with openings, for example a non-woven nylon or polyester mesh, of the appropriate thickness of say 0.1 mm, between the microporous membrane and the active surface of the sensor of the sensing device.

For measuring the concentration of dissolved gases in the thick liquid, the microporous membrane may be a hydrophobic membrane made of polypropylene or PTFE. The corresponding sensing device might then be a conventional dissolved has sensing device having an electrode which is responsive to a selected gaseous species, such as oxygen.

If the thick liquid is to be tested for the concentration of an ionic species, such as sodium, potassium, or hydrogen if pH is relevant, the microporous membrane may be a standard dialysis membrane such as Cuprophan, which is made of cellulose and is biocompatible and has a high permeability to electrolytes, particularly blood electrolytes. In this case the corresponding sensing device may be an ISFET having one or more gate electrodes coated with a material which is permeable substantially only to the selected ionic species.

In each case appropriate electrical or electronic circuitry will be connected to the sensing device to provide a sensible or recorded output corresponding to the concentration of the selected species.

The apparatus thus provides substantially continuous monitoring with good response times, infrequent recalibration, and no wasted thick liquid. Disposable components involved are of low cost, and particularly as the sensing device is not directly exposed to the thick liquid, it may be possible for it to be reused.

The construction and use of apparatus for measuring the concentration of an electrolyte in blood, in accordance with the present invention is illustrated diagrammatically in the accompanying drawings, in which:

FIG. 1 is a diagrammatic axial section through a blood line connector fitted with the apparatus;

FIG. 2 is an axial section taken perpendicular to the plane of the section of FIG. 1; and.

FIG. 3 is an enlargement of FIG. 1.

A blood line connector 4, forming a conduit for blood in a blood circuit has a hole in its wall covered by a microporous barrier membrane 5. Externally of the connector 4, the membrane 5 is covered by a measuring cell consisting essentially of an ISFET 6, gate electrodes 7 of which are spaced from the membrane 5 by means of a spacer 8 of an open non-woven fabric substantially 0.1 mm thick. The open volume within the spacer 8 forms the second chamber, which is essentially sealed except for inlet and outlet ducts 9, through which the clean fluid may be passed to flush the chamber but which may be closed by valves 10 to isolate the second chamber during a test. The electrodes 7 are coated with a material permeable to a selected ionic species.

In use the blood line is used in extracorporeal circulation, as in open heart surgery, haemodialysis or plasmapheresis. The cell is designed so the blood passes rapidly across one side of the barrier membrane, at the conventional output rate of 2-5 l/min, washing one side of the membrane, and preventing build up of blood proteins, platelets etc. In addition, diffusion of gases or ionic species across the barrier membrane is facilitated by the rapid flow of blood.

I claim:

1. Apparatus for testing the concentration of a selected atomic scale species in a thick liquid, the apparatus comprising a first chamber which contains, in use, a thick liquid under test, the chamber being at least partly defined by one face of a microporous dialysis membrane which is permeable to atomic scale species; and a measuring cell incorporating a second chamber which is arranged to be filled with a clean liquid and which is at least partly defined by an opposite face of the membrane whereby atomic scale species in the thick liquid under test diffuse through the membrane and are present in a clean liquid in a concentration related to that at which they exist in a thick liquid under test; the cell also incorporating a sensing device having an active surface which is responsive substantially only to a selected species and which comprises an electrode in communication with the clean liquid in the second chamber, said electrode being coated with a material which is permeable substantially only to a selected ionic species whereby the device provides an output related to the concentration of a selected species.

2. Apparatus according to claim 1 wherein the microporous membrane and the active surface of the sensor are spaced by substantially 0.1 mm.

3. Apparatus according to claim 1 wherein the second chamber is provided with inlet and outlet ducts for flushing the second chamber with clean liquid.

4. Apparatus according to claim 1 wherein the sensor is a dissolved gas sensing device having an electrode which is responsive to a selected gaseous species.

5. Apparatus according to claim 1 wherein the sensor is an ISFET having one or more gate electrodes coated with a material which is permeable substantially only to a selected ionic species.

6. Apparatus according to claim 1, for testing the concentration of dissolved gases in the thick liquid, wherein the microporous membrane is a hydrophobic membrane made of polypropylene or PTFE.

7. Apparatus according to claim 6, wherein the sensor is a dissolved gas sensing device having an electrode which is responsive to a selected gaseous species.

8. Apparatus according to claim 1 for testing the concentration of an ionic species, wherein the microporous membrane is a dialysis membrane.

9. Apparatus according to claim 8, wherein the sensor is an ISFET having one or more gate electrodes coated with a material which is permeable substantially only to the selected ionic species.

10. Apparatus according to claim 1, wherein the microporous membrane and the active surface of the sensor, which face one another, are spaced by a spacer formed with opening means which provide the second chamber.

11. Apparatus according to claim 10, wherein the spacer is a non-woven nylon or polyester mesh.

12. Apparatus according to claim 10 for testing the concentration of an ionic species, wherein the microporous membrane is a dialysis membrane.

13. Apparatus according to claim 1, wherein the first chamber is a blood line connector, having in its wall an opening means which is spanned by the microporous membrane, the cell being mounted on the outside of the connector overlying the membrane.

14. Apparatus according to claim 13 wherein the microporous membrane and the active surface of the sensor, which face one another, are spaced by a spacer formed with openings which provide the second chamber.

15. Apparatus according to claim 13 wherein the second chamber is provided with inlet and outlet ducts for flushing the second chamber with clean liquid.

16. Apparatus according to claim 15 wherein the microporous membrane and the active surface of the sensor which face one another, are spaced by a spacer formed with opening means which provide the second chamber.

17. Apparatus according to claim 15, wherein the inlet and outlet ducts are closeable to seal the interior of the cell during test.

18. Apparatus according to claim 17 wherein the microporous membrane and the active surface of the sensor, which face one another, are spaced by a spacer formed with opening means which provide the second chamber.

19. A method of testing the concentration of a selected atomic scale species in a flow of natural whole blood in an extracorporeal circuit, the method comprising continuously circulating the blood through a conduit having in its wall an aperture spanned by a microporous barrier membrane which is permeable to atomic scale species, but impermeable to proteins and other blood components of similar and larger size, whereby unselected atomic scale species pass through the barrier membrane into a measuring cell containing a clean liquid; sensing the concentration of the selected species in the clean liquid by means of a sensing device, which is responsive substantially only to the selected species, said device comprising an electrode coated with a material which is permeable substantially only to a selected ionic species; and providing an output related to the concentration of the selected species.

20. A method according to claim 19, wherein the sensor comprises an electrode coated with a material, which is permeable substantially only to a selected ionic species under test, but which is foulable by blood components retained by the barrier membrane.

* * * * *